(12) United States Patent
Ito et al.

(10) Patent No.: US 6,284,226 B1
(45) Date of Patent: Sep. 4, 2001

(54) AEROSOL COMPOSITION CONTAINING MIDDLE-CHAIN FATTY ACID TRIGLYCERIDE DISPERSANT

(75) Inventors: Hideki Ito, Izumisano; Masahiro Tsuji, Hashimoto; Hiromitu Yoshida, Kyoto; Fumio Shimojo, Kawanishi, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/380,601

(22) PCT Filed: Mar. 14, 1997

(86) PCT No.: PCT/JP97/00829

§ 371 Date: Sep. 14, 1999

§ 102(e) Date: Sep. 14, 1999

(87) PCT Pub. No.: WO98/41191

PCT Pub. Date: Sep. 24, 1998

(51) Int. Cl.[7] .................................................. A61K 9/12
(52) U.S. Cl. .............................. 424/45; 424/46; 514/826; 514/18
(58) Field of Search ........................ 424/45, 46; 514/826, 514/18

(56) References Cited

FOREIGN PATENT DOCUMENTS

| | | | |
|---|---|---|---|
| 518600 | * | 12/1992 | (JP) . |
| 93/21215 | * | 10/1993 | (WO) . |
| 95/00536 | * | 1/1995 | (WO) . |
| 95/04551 | * | 2/1995 | (WO) . |

* cited by examiner

Primary Examiner—Raj Bawa
(74) Attorney, Agent, or Firm—Oblon, Spivak, McClelland, Maier & Neustadt, P.C.

(57) ABSTRACT

An aerosol product comprising the following compound (A), a middle-chain fatty acid triglyceride and a liquefied hydrofluoroalkane is provided. In the production of an aerosol product using a liquefied hydrofluoroalkane as propellant, the use of a middle-chain fatty acid triglyceride as dispersant insures good dispersion of compound (A) in the propellant.

The result is an aerosol product free from variation in the dispensed dose of compound (A).

(A)

AEROSOL COMPOSITION CONTAINING MIDDLE-CHAIN FATTY ACID TRIGLYCERIDE DISPERSANT

TECHNICAL FIELD

This invention relates to an aerosol composition comprising the following compound of formula (A) and finds application in the field of health care.

(A)

[Chemical structure of compound (A)]

BACKGROUND ART

The compound of the above formula (A) (hereinafter referred to briefly as compound (A)) is described in WO 93/21215. Being a neurokinin receptor antagonist, the compound is useful for the therapy of bronchial asthma and chronic bronchitis, among other diseases.

This compound (A) in the finely divided bulk state is apt to undergo agglomeration and caking so that when processed into a powder inhalant, the bulk substance cannot be sufficiently delivered to the target bronchi.

An apparently reasonable approach would be dispersing it in an aerosol propellant for administration. However, when dispersed in an aerosol propellant, compound (A) remains dispersed only for a short while following shaking of the package but soon begins to be segregated from the propellant, with the result that by the time of dispensing for administration the compound (A) will have separated out to a marked extent to frustrate sufficient medication owing to a variation in the administered dose.

The conventional aerosol product employs one or more kinds of liquefied chlorofluorocarbons (hereinafter referred to collectively as CFC) as a propellant and contains a finely divided powder of the active substance dispersed in CFC with the aid of a suitable dispersant.

However, CFC is involved in destruction of the ozonosphere and, in many countries, a total ban on its use is expected to be enforced within this century at earliest. Therefore, as substitute aerosol propellants, the use of liquefied hydrofluoroalkanes (hereinafter referred to sometimes collectively as HFA) is being evaluated. Being a better choice from the standpoint of preservation of the ozonosphere, HFA has the drawback that the dispersants (e.g. soybean lecithin) heretofore used in combination with CFC are not soluble in HFA at all, with the result that compound (A) cannot be dispersed in HFA and, hence, no satisfactory aerosol product of compound (A) can be provided.

DISCLOSURE OF THE INVENTION

The inventors of this invention did intensive investigations to solve the above problem and found that compound (A) can be uniformly dispersed in HFA by using a middle-chain fatty acid triglyceride as dispersant so that a satisfactory aerosol with little-variation in the dose dispensed can be obtained.

The aerosol composition according to this invention comprises said compound of formula (A), a middle-chain fatty acid triglyceride and a liquefied hydrofluoroalkane. Preferably, the aerosol composition of this invention contains polyvinylpyrrolidone in addition to said ingredients.

In the aerosol composition of this invention, the concentration of the active ingredient compound (A) is 0.05~10 w/v %, preferably 0.1~5 w/v %, and the compound (A) is used generally after size reduction to about 0.5~5 µm in particle diameter.

In the aerosol composition of this invention, the middle-chain fatty acid triglyceride used as the dispersant for compound (A) is chiefly the triglyceride of saturated fatty acids [$CH_3(CH_2)_nCOOH$, n=4~10], and many proprietary products, such as Miglyol 812 (trademark, Dynamit Nobel), Panacete 810 (trademark, NOF Corporation), Coconade (trademark, Kao Corporation), Myritol GM (trademark, Henckell Hakusui) and ODO (trademark, The Nisshin Oil Mills, Ltd.), are commercially available and can be utilized.

The formulating amount of the middle-chain fatty acid triglyceride is generally 0.01~1 w/v %, preferably 0.05~0.5 w/v %.

The liquefied hydrofluoroalkane for use as propellant in the aerosol composition of this invention includes but is not limited to HFA134a (1,1,1,2-tetrafluoroethane: $CH_2FCF_3$) and HFA227 (1,1,1,2,3,3,3-heptafluoropropane: $CF_3CHCF_3$) and those liquefied hydrofluoroalkanes can be used each alone or as a mixture.

For a further improved dispersibility of compound (A), the aerosol composition of this invention is preferably supplemented with 0.001~0.5 w/v %, more preferably 0.01~0.1 w/v %, of polyvinylpyrrolidone.

Furthermore, the aerosol composition of this invention may contain the conventional dispersant such as polyvinyl alcohol, sorbitan fatty acid ester, polyoxyethylene-sorbitan fatty acid ester (e.g. Tween 20, Span 85, etc.), fatty acid ester, polyethylene glycol fatty acid ester, polyoxyethylene alkyl ether, sucrose ester, lecithin, HCO-60 (polyoxyethylene-hydrogenated castor oil), oleic acid or isopropyl myristate in a proportion of 0.0001~0.01 w/v %.

The process for producing the aerosol composition of this invention is now described. Compound (A), comminuted in the routine manner in advance, and a middle-chain fatty acid triglyceride, optionally as well as polyvinylpyrrolidone, are added to a liquefied hydrofluoroalkane at −20° C. and the resulting composition is distributed into aerosol containers (usually aluminum cans) with sufficient stirring.

Then, each aerosol container is fitted with a valve for dispensing.

As an alternative, after addition of the above ingredients to the liquefied hydrofluoroalkane at atmospheric temperature and sufficient stirring, the resulting composition is distributed into aerosol containers fitted with valves under an elevated pressure of 20~30 atmospheres.

The dispensing amount of the aerosol product of this invention per actuation is 25~150 µl and the composition is dispensed by 1~4 actuations per dose once to 4 times daily.

INDUSTRIAL APPLICABILITY

When soybean lecithin was used as dispersant as in Comparative Example 1 which appears below, compound (A) could not be dispersed at all in the propellant HFA-227. However, when a middle-chain fatty acid triglyceride (Miglyol 812) was used as dispersant as in Example 1 of this invention, compound (A) could be well dispersed. Thus, in accordance with the aerosol composition of this invention, the active ingredient compound (A) can be provided as a uniform dispersion in the propellant. Accordingly there can be provided an aerosol product which shows no variation in the dose dispensed, thus being of use in the therapy of bronchial asthma and chronic bronchitis.

COMPARATIVE EXAMPLE 1

Compound (A) was comminuted to 5 μm or less in the routine manner and added, together with soybean lecithin, to HFA-227 precooled to −20°C., followed by stirring. The amounts of the respective ingredients in HFA-227 (5 ml) were as follows.

| Compound (A) | 50 mg |
| Soybean lecithin | 5 mg |
| HFA-227 | 5 ml |

EXAMPLES

Example 1

Compound (A) was comminuted to 5 μm or less in the routine manner and added, together with Miglyol 812, to HFA-227 precooled to −20°C. The resulting mixture was distributed under sufficient agitation into aerosol containers and valves were set in position to provide an aerosol product containing the following ingredients per package (5 ml).

| Compound (A) | 50 mg |
| Miglyol 812 | 5 mg |
| HFA-227 | 5 ml |

Example 2

Compound (A) was comminuted to 5 μm or less in the routine manner and added, together with Miglyol 812, to HFA-227, followed by sufficient stirring. Then, the resulting mixture was distributed into aerosol containers fitted with valves under 20 atmospheres at room temperature to provide an aerosol product containing the same ingredients in the same amounts as in Example 1.

Example 3

An aerosol product of the following composition was prepared in otherwise the same manner as in Example 1.

| Compound (A) | 50 mg |
| Miglyol 812 | 10 mg |
| HFA-134a | 5 ml |

Example 4

Compound (A) was comminuted to 5 μm or less in the routine manner and added, together with Panacete 810 and polyvinylpyrrolidone, to HFA-227, followed by sufficient stirring.

Thereafter, the procedure used in example 2 was repeated to provide an aerosol product of the following composition

| Compound (A) | 50 mg |
| Panacete 810 | 5 mg |
| Polyvinylpyrrolidone | 1.5 mg |
| HFA-227 | 5 ml |

What is claimed is:

1. An aerosol composition comprising an active amount of a compound of the following formula (A):

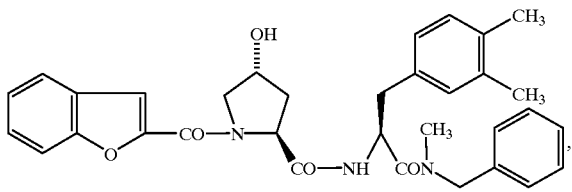

a liquefied hydrofluoroalkane, and a middle-chain fatty acid triglyceride in an amount sufficient to disperse said compound of formula (A) in said liquefied hydrofluoroalkane.

2. The aerosol composition of claim 1 further comprising polyvinylpyrrolidone.

3. The aerosol composition of claim 1 wherein the liquefied hydrofluoroalkane is selected from the group consisting of HFA 134a, HFA227, and mixtures thereof.

4. The aerosol composition of claim 2, wherein the liquified hydrofluoroalkane is selected from the group consisting of HFA 134a, HFA227, and mixtures thereof.

5. The aerosol composition of claim 1, wherein said active amount of said compound of formula (A) is about 0.05 to 10 w/v %.

6. The aerosol composition of claim 5, wherein said active amount is about 0.1 to about 5 w/v %.

7. The aerosol composition of claim 1, wherein said middle-chain fatty acid triglyceride is present in an amount of about 0.01–1 w/v %.

8. The aerosol composition of claim 5, wherein said middle-chain fatty acid triglyceride is present in an amount of about 0.01–1 w/v %.

9. The aerosol composition of claim 6, wherein said middle-chain fatty acid triglyceride is present in an amount of about 0.01–1 w/v %.

10. The aerosol composition of claim 1, wherein said middle-chain fatty acid triglyceride is present in an amount of about 0.05–0.5 w/v %.

11. The aerosol composition of claim 5, wherein said middle-chain fatty acid triglyceride is present in an amount of about 0.05–0.5 w/v %.

12. The aerosol composition of claim 6, wherein said middle-chain fatty acid triglyceride is present in an amount of about 0.05–0.5 w/v %.

13. The aerosol composition of claim 1, wherein said middle-chain fatty acid triglyceride has the formula $CH_3(CH_2)_nCOOH$, wherein n is about 4–10.

14. The aerosol composition of claim 5, wherein said middle-chain fatty acid triglyceride has the formula $CH_3(CH_2)_nCOOH$, wherein n is about 4–10.

15. The aerosol composition of claim 6, wherein said middle-chain fatty acid triglyceride has the formula $CH_3(CH_2)_nCOOH$, wherein n is about 4–10.

16. The aerosol composition of claim 7, wherein said middle-chain fatty acid triglyceride has the formula $CH_3(CH_2)_n COOH$, wherein n is about 4–10.

17. The aerosol composition of claim 8, wherein said middle-chain fatty acid triglyceride has the formula $CH_3(CH_2)_n COOH$, wherein n is about 4–10.

18. The aerosol composition of claim 9, wherein said middle-chain fatty acid triglyceride has the formula $CH_3(CH_2)_n COOH$, wherein n is about 4–10.

19. The aerosol composition of claim 10, wherein said middle-chain fatty acid triglyceride has the formula $CH_3(CH_2)_n COOH$, wherein n is about 4–10.

20. The aerosol composition of claim 11, wherein said middle-chain fatty acid triglyceride has the formula $CH_3(CH_2)_n COOH$, wherein n is about 4–10.

\* \* \* \* \*